(12) United States Patent
Capacci-Daniel et al.

(10) Patent No.: US 8,987,459 B2
(45) Date of Patent: Mar. 24, 2015

(54) COMPOUNDS FOR THE TREATMENT OF CONDITIONS ASSOCIATED WITH DGAT1 ACTIVITY

(71) Applicants: Christina Capacci-Daniel, Silver Spring, MD (US); Marilyn DeLaCruz, Matawan, NJ (US); Baoqing Gong, Morris Plains, NJ (US); Akash Jain, Burlington, MA (US); Yansong Lu, Edison, NJ (US); Lijun Zhang, Shanghai (CN)

(72) Inventors: Christina Capacci-Daniel, Silver Spring, MD (US); Marilyn DeLaCruz, Matawan, NJ (US); Baoqing Gong, Morris Plains, NJ (US); Akash Jain, Burlington, MA (US); Yansong Lu, Edison, NJ (US); Lijun Zhang, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/152,282

(22) Filed: Jan. 10, 2014

(65) Prior Publication Data

US 2014/0200246 A1 Jul. 17, 2014

Related U.S. Application Data

(60) Provisional application No. 61/751,443, filed on Jan. 11, 2013.

(51) Int. Cl.
*C07D 413/00* (2006.01)
*C07D 413/12* (2006.01)
*A61K 31/4439* (2006.01)
*A61K 45/06* (2006.01)

(52) U.S. Cl.
CPC .......... *C07D 413/12* (2013.01); *A61K 31/4439* (2013.01); *A61K 45/06* (2013.01)
USPC ...................................................... 546/271.7

(58) Field of Classification Search
CPC ..................................................... C07D 413/12
USPC ...................................................... 546/271.7
See application file for complete search history.

(56) References Cited

FOREIGN PATENT DOCUMENTS

| WO | 2007/126957 | 11/2007 | | |
|----|-------------|---------|---|---|
| WO | 2013/169648 | 11/2013 | | |
| WO | WO 2013169648 | * 11/2013 | ........... | A61K 31/444 |

OTHER PUBLICATIONS

Denzinger, World Pharmaceutical Frontiers, 2:90 (2011).

* cited by examiner

*Primary Examiner* — Nizal Chandrakumar
(74) *Attorney, Agent, or Firm* — Joshua Roth

(57) ABSTRACT

The present invention relates to novel crystalline forms of salts of 2-((1R,4R)-4-(4-(5-(benzo[d]oxazol-2-ylamino)pyridin-2-yl)phenyl)cyclohexyl)acetic acid and their use in the treatment or prevention of a condition or a disorder associated with DGAT1 activity in animals, particularly humans.

3 Claims, 9 Drawing Sheets

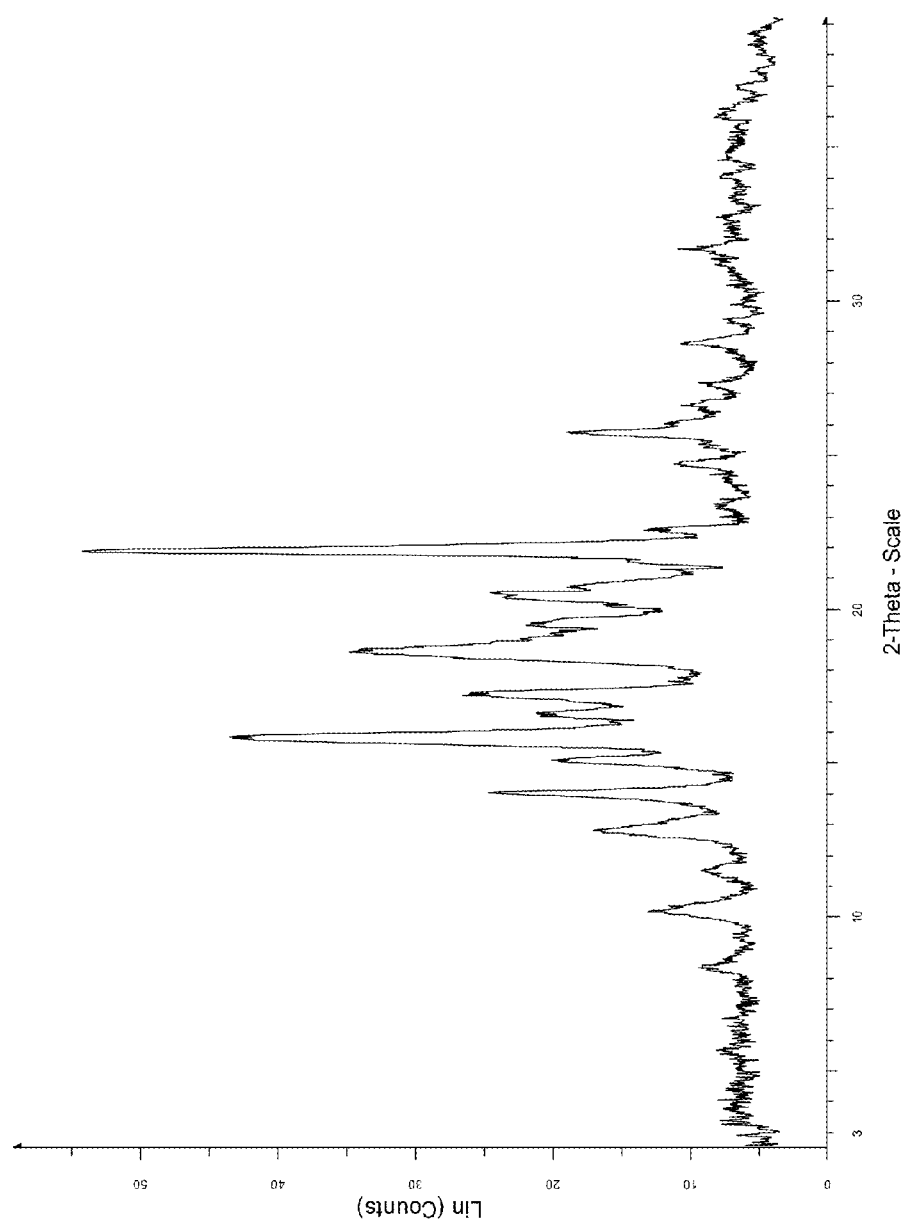
Fig. 1: XRPD of the Meglumine Salt of 2-((1R,4R)-4-(4-(5-(benzo[d]oxazol-2-ylamino)pyridin-2-yl)phenyl)cyclohexyl)acetic acid Polymorph Form A.

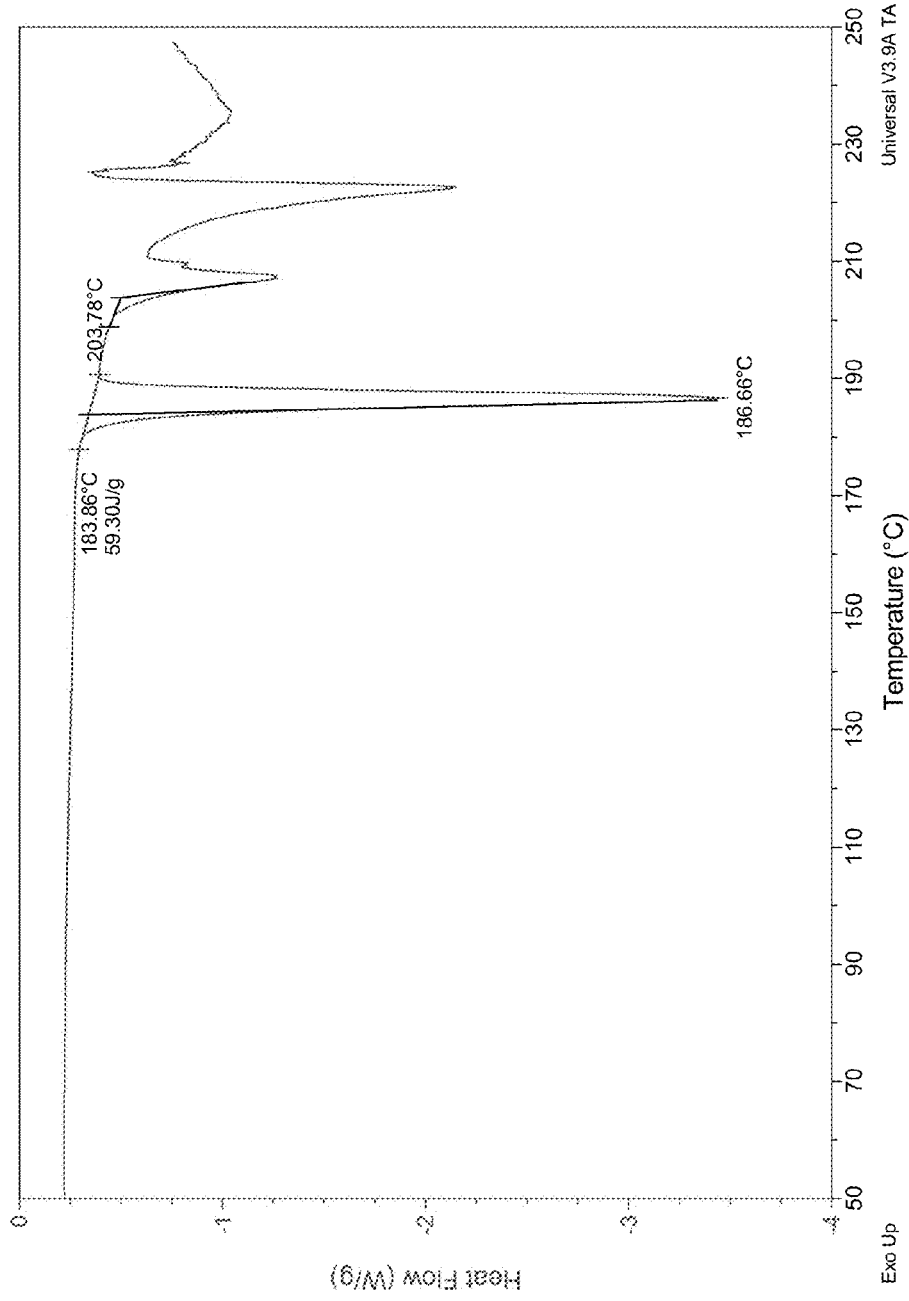
Fig. 2: DSC Thermogram of the Meglumine Salt of 2-((1R,4R)-4-(4-(5-(benzo[d]oxazol-2-ylamino)pyridin-2-yl)phenyl)cyclohexyl)acetic acid Polymorph Form A.

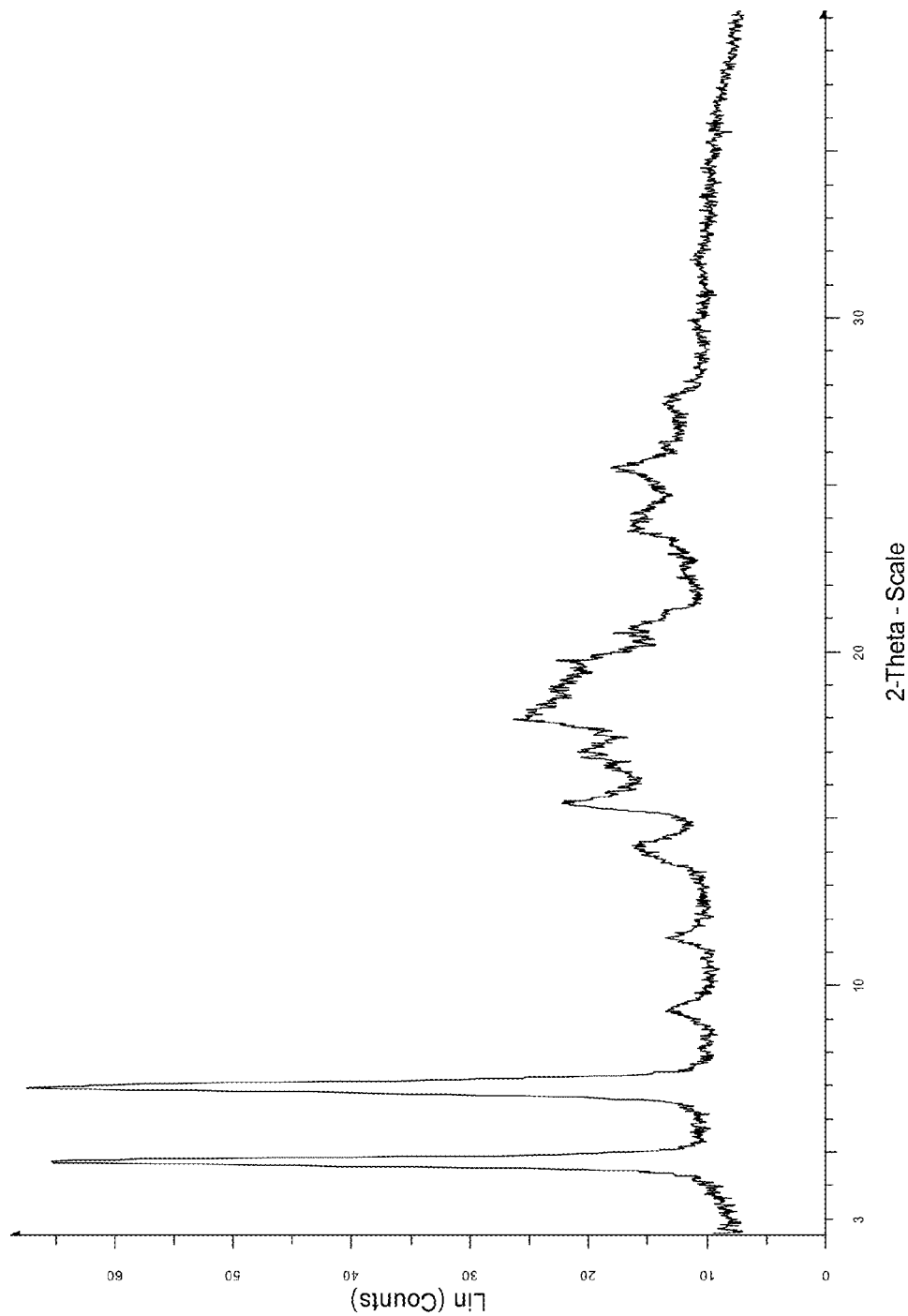
Fig. 3: XRPD of the Meglumine Salt of 2-((1R,4R)-4-(4-(5-(benzo[d]oxazol-2-ylamino)pyridin-2-yl)phenyl)cyclohexyl)acetic acid Polymorph Form B.

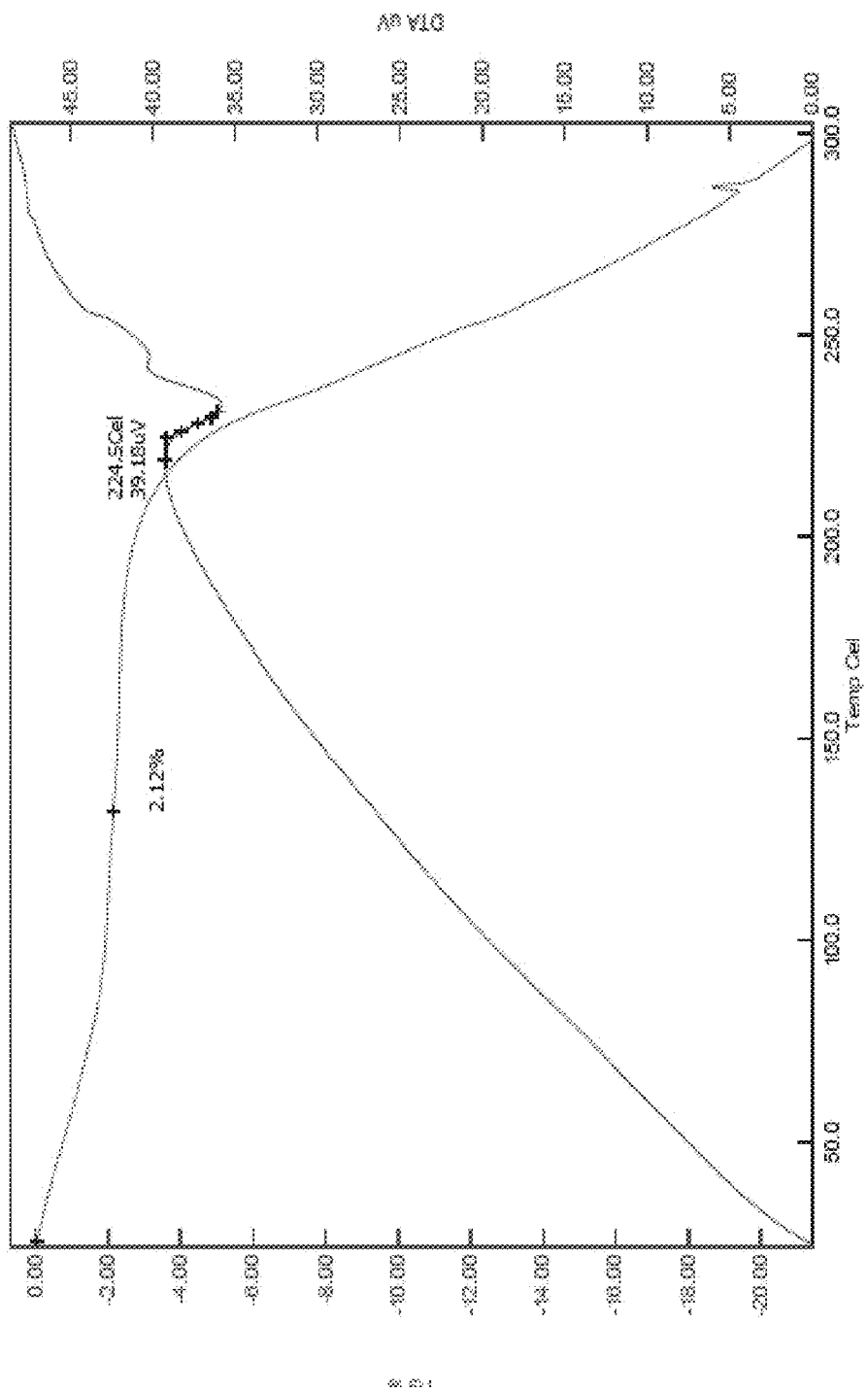
Fig. 4: TG/DTA Thermograph of the Meglumine Salt of 2-((1R,4R)-4-(4-(5-(benzo[d]oxazol-2-ylamino)pyridin-2-yl)phenyl)cyclohexyl)acetic acid Polymorph Form B.

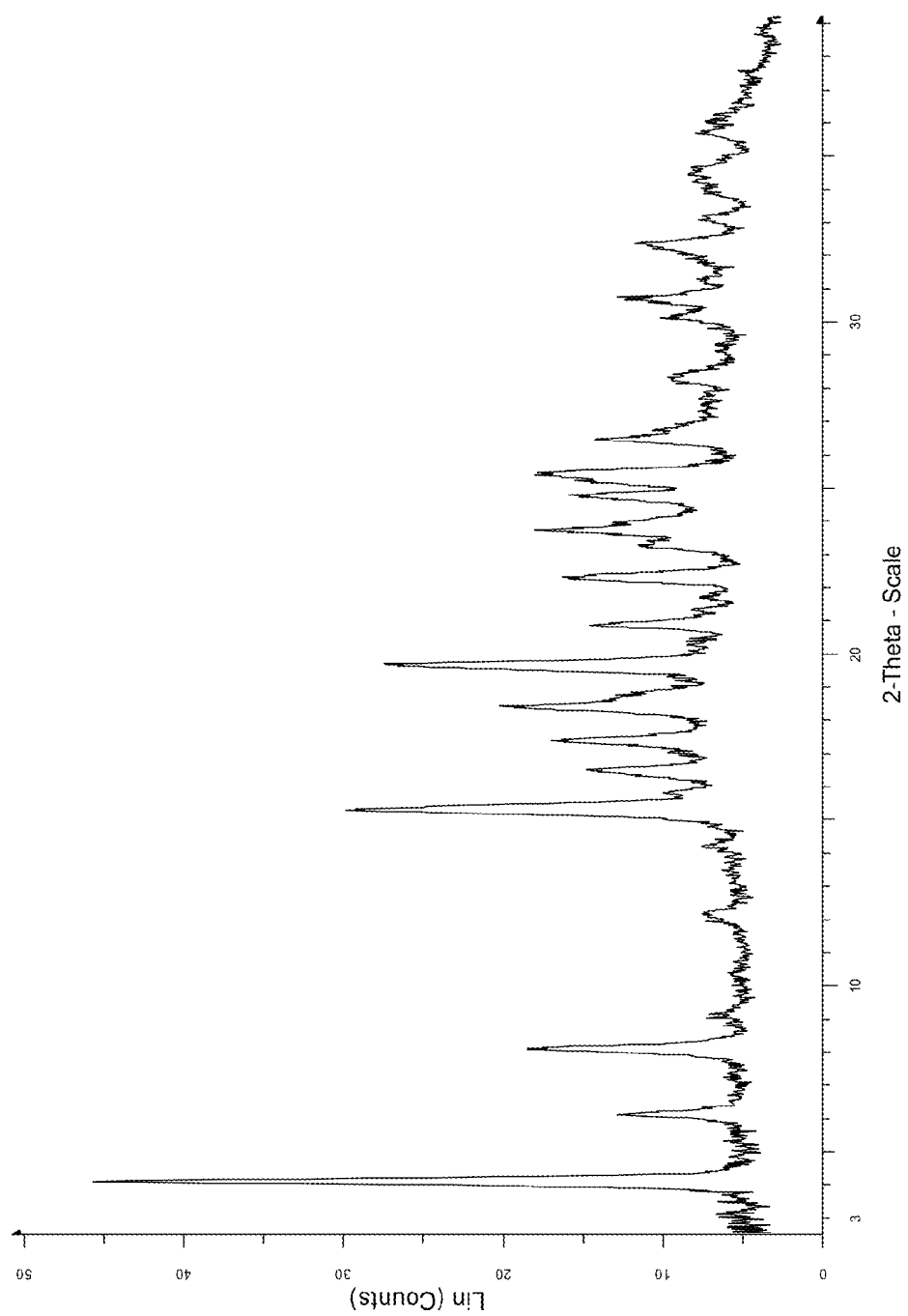
Fig. 5: XRPD of the Meglumine Salt of 2-(((1R,4R)-4-(4-(5-(benzo[d]oxazol-2-ylamino)pyridin-2-yl)phenyl)cyclohexyl)acetic acid Polymorph Form C.

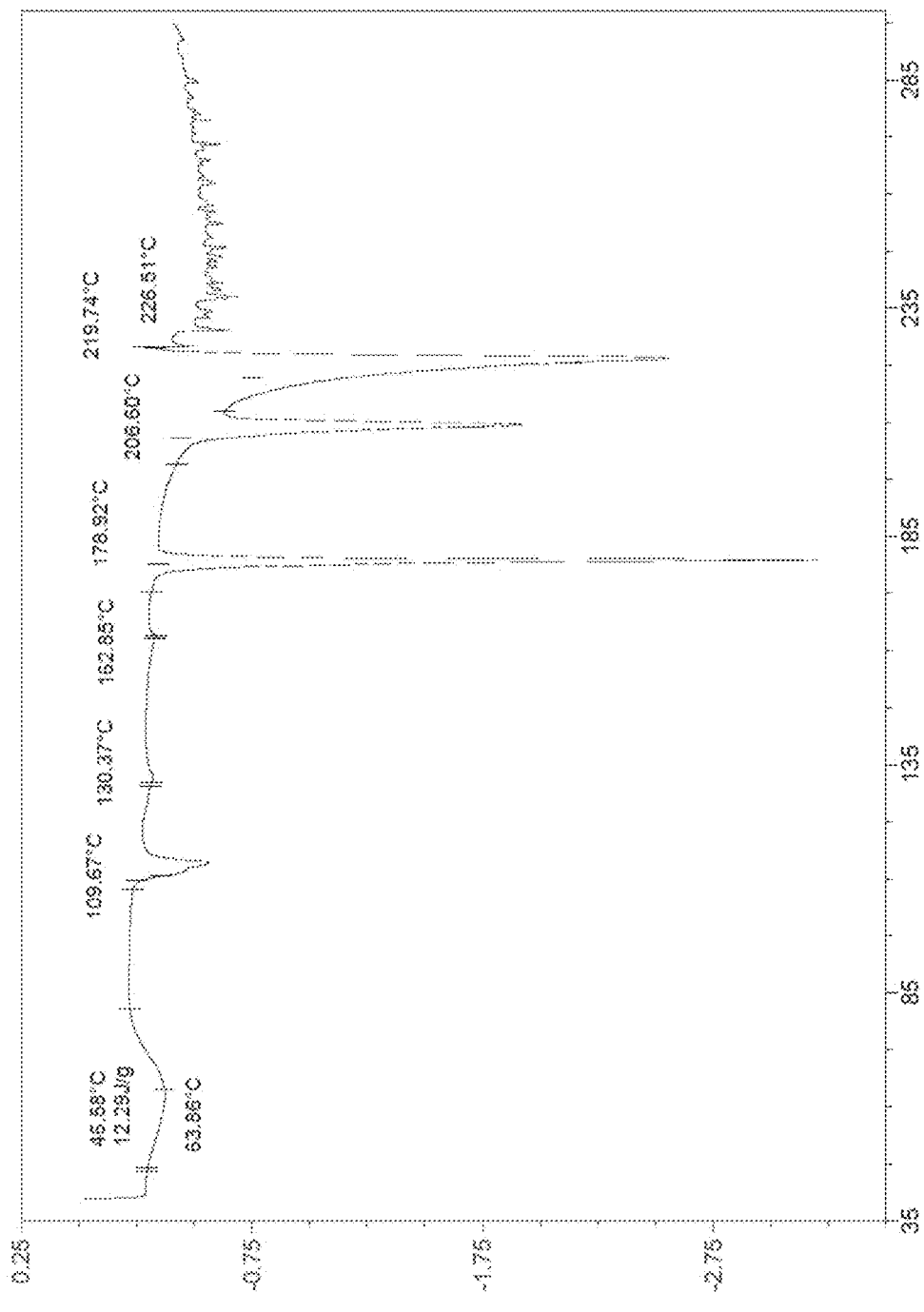
Fig. 6: DSC Thermogram of the Meglumine Salt of 2-((1R,4R)-4-(4-(5-(benzo[d]oxazol-2-ylamino)pyridin-2-yl)phenyl)cyclohexyl)acetic acid Polymorph Form C.

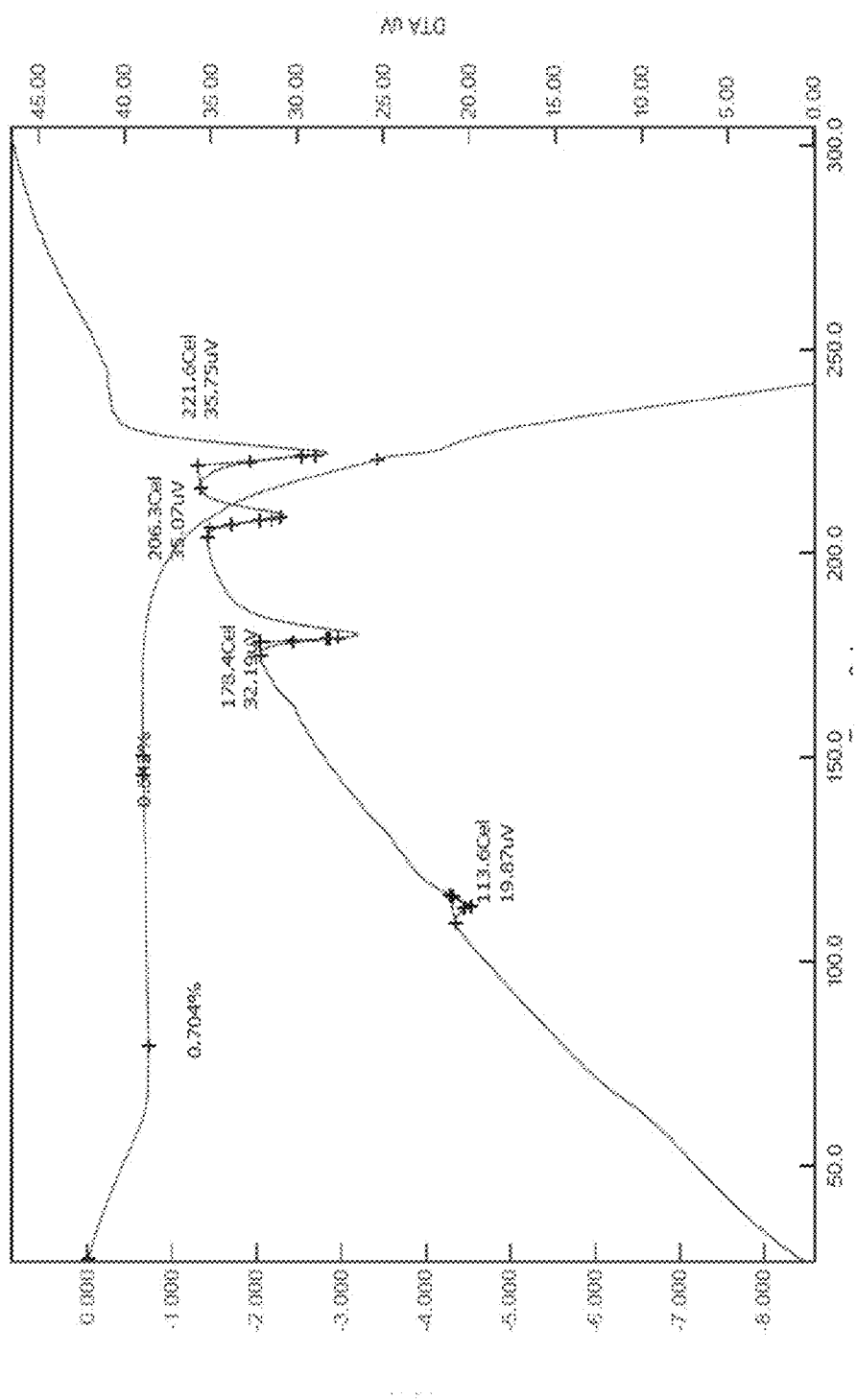
Fig. 7: TG/DTA Thermogram of the Meglumine Salt of 2-((1R,4R)-4-(4-(5-(benzo[d]oxazol-2-ylamino)pyridin-2-yl)phenyl)cyclohexyl)acetic acid Polymorph Form C.

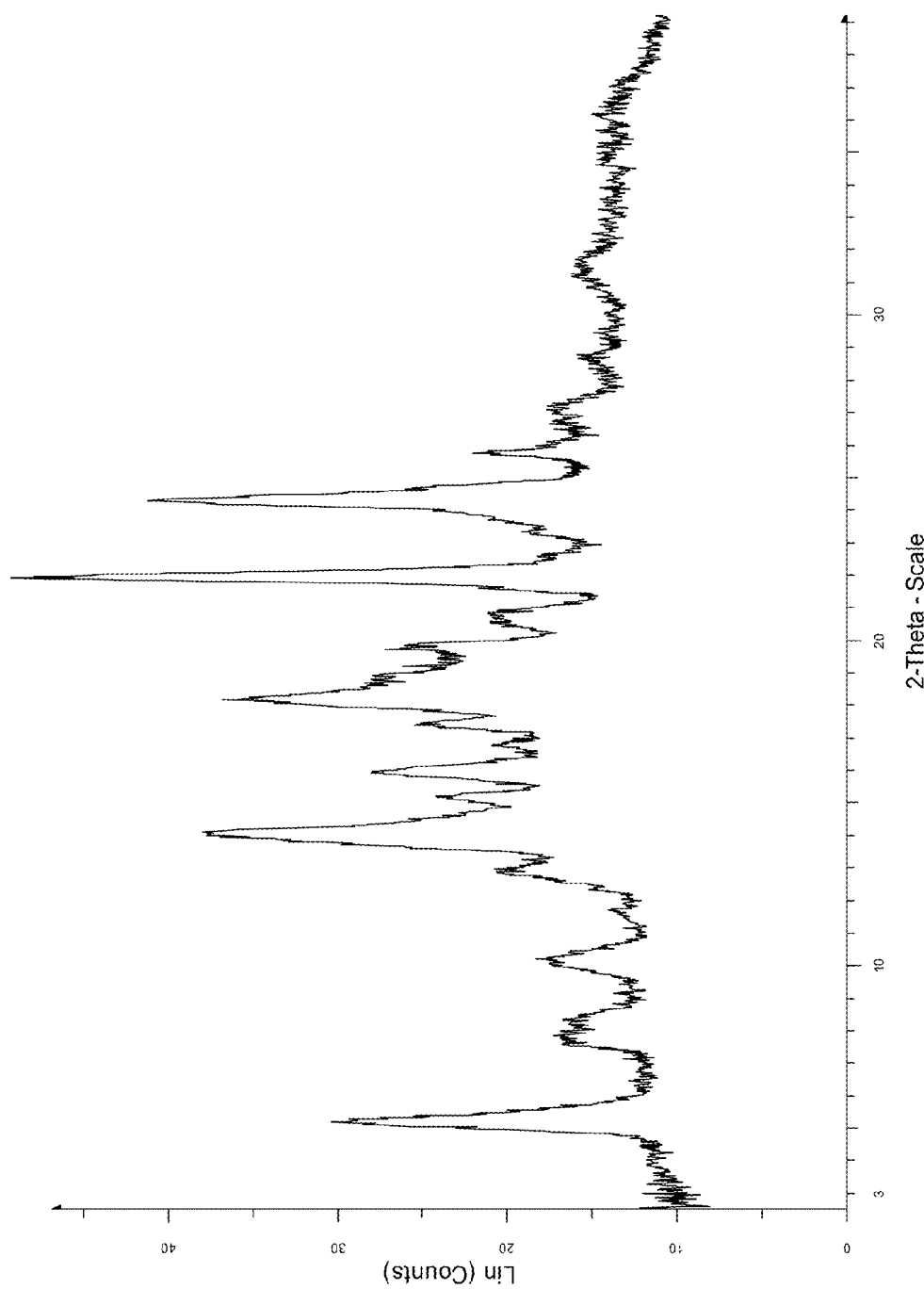
Fig. 8: XRPD of the Meglumine Salt of 2-((1R,4R)-4-(4-(5-(benzo[d]oxazol-2-ylamino)pyridin-2-yl)phenyl)cyclohexyl)acetic acid Polymorph Form H.

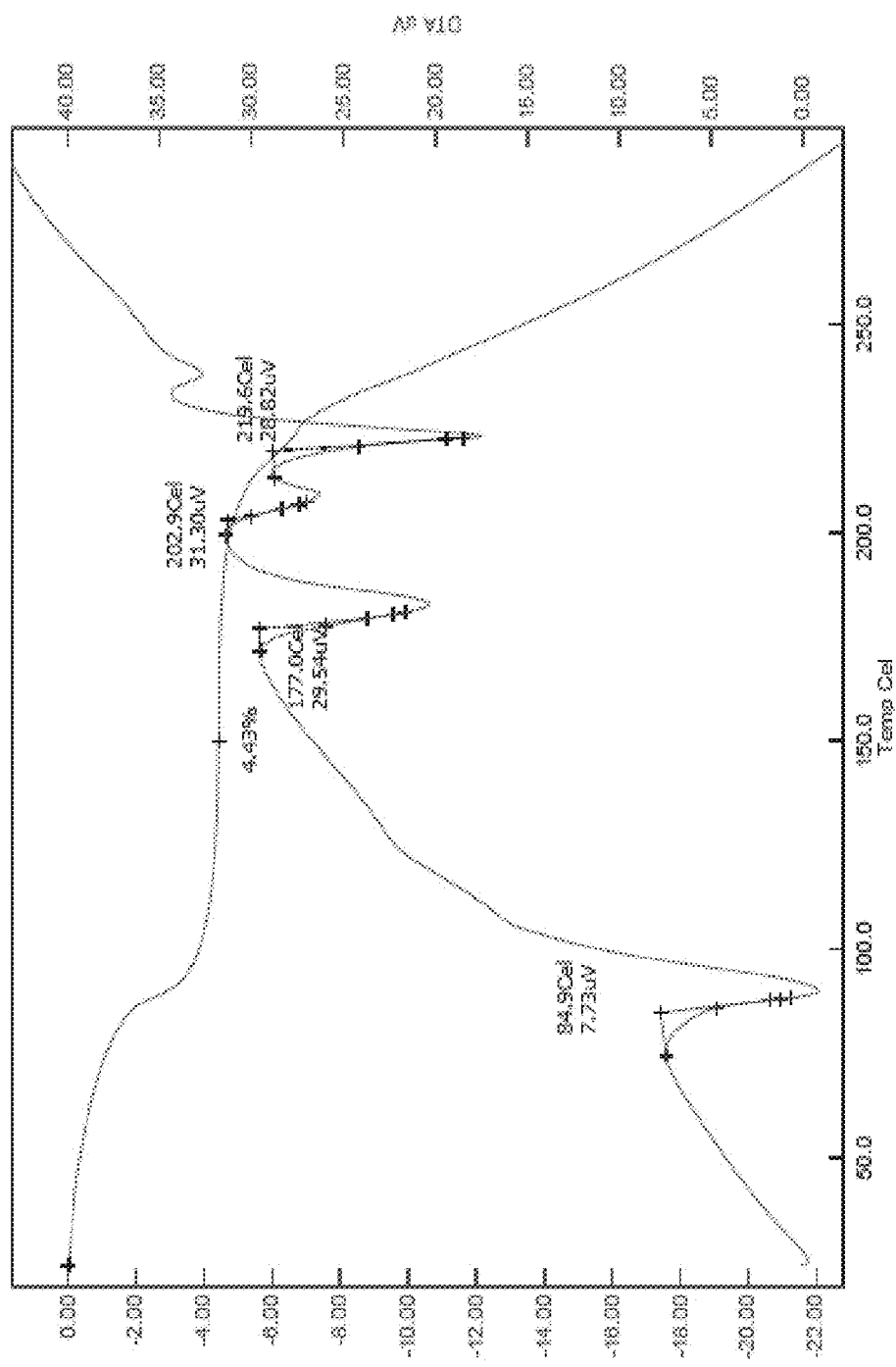
Fig. 9: TG/DTA Thermogram of the Meglumine Salt of 2-((1R,4R)-4-(4-(5-(benzo[d]oxazol-2-ylamino)pyridin-2-yl)phenyl)cyclohexyl)acetic acid Polymorph Form C.

COMPOUNDS FOR THE TREATMENT OF CONDITIONS ASSOCIATED WITH DGAT1 ACTIVITY

FIELD OF THE INVENTION

The present invention relates to novel solid state salt forms of 2-((1R,4R)-4-(4-(5-(benzo[d]oxazol-2-ylamino)pyridin-2-yl)phenyl)cyclohexyl)acetic acid and to pharmaceutical compositions comprising these solid salt forms, and to processes for making such novel forms. The invention further relates to the use of the novel solid state salt forms and the compositions thereof, alone or in combination with one or more therapeutic agents, in the treatment of various conditions, particularly in the treatment of a condition or a disorder associated with DGAT1 activity.

BACKGROUND OF THE INVENTION

Obesity can be viewed as an energy balance disorder, arising when energy input exceeds energy output, with most of the excess calories converted into triglycerides and stored in the adipose tissue. Medications currently approved for the treatment of obesity attempts to restore energy balance primarily by decreasing energy input by either suppressing appetite or interfering with lipid absorption in the small intestine. Because of the rapid increase in the prevalence of obesity worldwide and the lack of efficacy of current medical therapies, novel pharmacologic therapies for obesity are required.

One potential therapeutic strategy involves inhibiting triglyceride synthesis. Although triglycerides are essential for normal physiology, excess triglyceride accumulation results in obesity and, particularly when it occurs in nonadipose tissues, is associated with insulin resistance. DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggest that a DGAT1 inhibitor has utility for the treatment of obesity and obesity-associated complications.

WO2007/126957 discloses a genus of compounds which are disclosed to be inhibitors of DGAT1, and therefore useful in the treatment of a condition or a disorder such as obesity, diabetes and related metabolic disorders. Example 5-23 of said document discloses the compound 2-((1R,4R)-4-(4-(5-(benzo[d]oxazol-2-ylamino)pyridin-2-yl)phenyl)cyclohexyl)acetic acid having the structural formula (I):

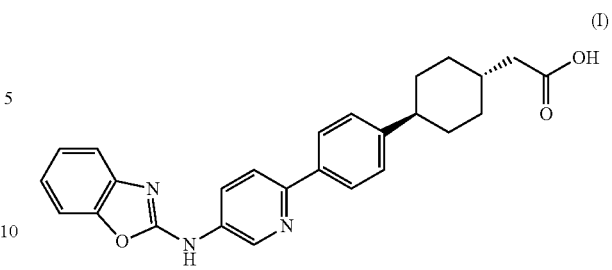

No salt forms of this compound where prepared and the free acid exhibited low intrinsic dissolution and low solubility making large scale manufacture and purification difficult.

It is thus important to provide the compound of formula (I) in a salt form and physical form which can be reliably prepared and purified on a large scale, and ideally is stable and does not degrade on storage. The salt form/physical form chosen must also be stable whilst the drug substance is being manufactured as a formulation which is suitable for the intended route of administration chosen. In that respect, it may be necessary to consider physical properties of the salt form in a particular physical form which lead to improved powder handling properties or higher bulk density. In particular, non-hygroscopicity is particularly important in order to obtain good flow characteristics.

The properties of the final product should also be predictable and reliably reproducible. For example, material which is obtained in an inconsistent manner, for example, where the water content differs from batch to batch, must be carefully monitored. This leads to added complications in the handling, manufacture, analysis and formulation of the drug substance.

Whilst one solid state form may exhibit properties which are considered suitable, another form may also have properties which, with the right measures in place, can lead to its successful development into a drug. The decision as to whether a compound is suitable for commercialization thus depends on finding a solid state form of the compound which has the right balance of desirable characteristics.

SUMMARY OF THE INVENTION

To improve the manufacturing and purification of 2-((1R,4R)-4-(4-(5-(benzo[d]oxazol-2-ylamino)pyridin-2-yl)phenyl)cyclohexyl)acetic acid various salt forms and various crystalline forms of the salts were prepared.

In one aspect, the present invention provides a salt form of the compound of formula (I). In one embodiment, the salt form is a meglumine salt of the compound of formula (I).

In another aspect, the invention provides the meglumine salt of 2-((1R,4R)-4-(4-(5-(benzo[d]oxazol-2-ylamino)pyridin-2-yl)phenyl)cyclohexyl)acetic acid, having the structural formula (Ia)

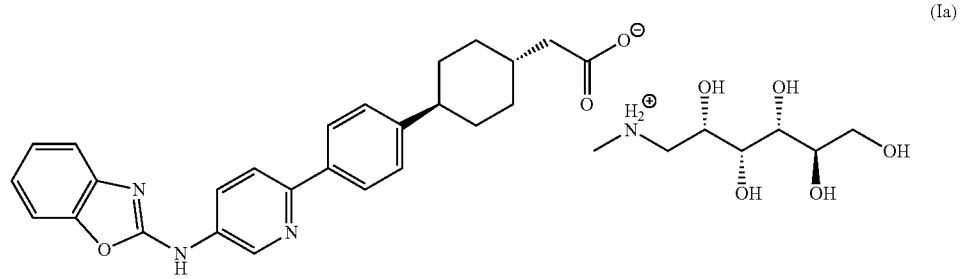

The meglumine salt of 2-((1R,4R)-4-(4-(5-(benzo[d]oxazol-2-ylamino)pyridin-2-yl)phenyl)cyclohexyl)acetic acid can be present in the form of various solid state forms, namely Form A, Form B, Form C or Form H.

In one embodiment, the invention provides meglumine salt of 2-((1R,4R)-4-(4-(5-(benzo[d]oxazol-2-ylamino)pyridin-2-yl)phenyl)cyclohexyl)acetic acid as shown in formula (Ia) in the form of Form A. In one embodiment, the invention provides meglumine salt of 2-((1R,4R)-4-(4-(5-(benzo[d]oxazol-2-ylamino)pyridin-2-yl)phenyl)cyclohexyl)acetic acid as shown in formula (Ia) in the form of Form B. In one embodiment, the invention provides meglumine salt of 2-((1R,4R)-4-(4-(5-(benzo[d]oxazol-2-ylamino)pyridin-2-yl)phenyl)cyclohexyl)acetic acid as shown in formula (Ia) in the form of Form C. In one embodiment, the invention provides meglumine salt of 2-((1R,4R)-4-(4-(5-(benzo[d]oxazol-2-ylamino)pyridin-2-yl)phenyl)cyclohexyl)acetic acid as shown in formula (Ia) in the form of Form H. Each solid state form may be characterised by an X-ray diffraction pattern as set forth in its corresponding Figure. The most significant peaks characteristic for each solid state form are given in the corresponding Table.

In another aspect of the invention, there is provided a pharmaceutical composition comprising a salt in the form of any one of the solid state forms, and one or more pharmaceutically acceptable carrier or excipient. In another aspect of the invention, the pharmaceutical composition comprises an additional therapeutic agent.

In a further aspect, there is provided a salt, preferably a meglumine salt of formula (Ia), in the form of any one of the solid state forms or a pharmaceutical composition as described above, for use in treating or preventing a condition or disorder associated with DGAT1 activity. There is also provided as one aspect of the invention, the use of such a salt or such a pharmaceutical composition for the manufacture of a medicament for treating or preventing a condition or disorder associated with DGAT1 activity.

In a further aspect, there is provided a method for treating or preventing a condition or disorder associated with DGAT1 activity, which method comprises administering to a subject in need thereof a therapeutically effective amount of a salt, preferably a meglumine salt of formula (Ia), in the form of any one of the solid state forms, or a therapeutically effective amount of the pharmaceutical composition described herein.

In a further aspect, the invention provides a process for making a meglumine salt form of the compound of formula (I).

In a further aspect, the invention provides a process for making a solid state form of the meglumine salt of 2-((1R,4R)-4-(4-(5-(benzo[d]oxazol-2-ylamino)pyridin-2-yl)phenyl)cyclohexyl)acetic acid as shown in formula (Ia). In one embodiment, the invention provides a process for making a salt represented by formula (Ia) which has the solid state form of Form A, Form B, Form C, or Form H.

Further aspects and embodiments of the disclosure are set forth in the following description and claims.

BRIEF DESCRIPTION OF THE FIGURES

FIG. 1 shows the X-ray powder diffraction pattern of the meglumine salt of 2-((1R,4R)-4-(4-(5-(benzo[d]oxazol-2-ylamino)pyridin-2-yl)phenyl)cyclohexyl)acetic acid Polymorph Form A.

FIG. 2 is a TG/DTA thermograph of polymorph Form A of the meglumine salt of 2-((1R,4R)-4-(4-(5-(benzo[d]oxazol-2-ylamino)pyridin-2-yl)phenyl)cyclohexyl)acetic acid.

FIG. 3 shows the X-ray powder diffraction pattern of the meglumine salt of 2-((1R,4R)-4-(4-(5-(benzo[d]oxazol-2-ylamino)pyridin-2-yl)phenyl)cyclohexyl)acetic acid Polymorph Form B.

FIG. 4 is a TG/DTA thermograph of polymorph Form B of the meglumine salt of 2-((1R,4R)-4-(4-(5-(benzo[d]oxazol-2-ylamino)pyridin-2-yl)phenyl)cyclohexyl)acetic acid.

FIG. 5 shows the X-ray powder diffraction pattern of the meglumine salt of 2-((1R,4R)-4-(4-(5-(benzo[d]oxazol-2-ylamino)pyridin-2-yl)phenyl)cyclohexyl)acetic acid Polymorph Form C.

FIG. 6 is a DSC thermogram of polymorph Form C of the meglumine salt of 2-((1R,4R)-4-(4-(5-(benzo[d]oxazol-2-ylamino)pyridin-2-yl)phenyl)cyclohexyl)acetic acid.

FIG. 7 is a TG/DTA thermograph of polymorph Form C of the meglumine salt of 2-((1R,4R)-4-(4-(5-(benzo[d]oxazol-2-ylamino)pyridin-2-yl)phenyl)cyclohexyl)acetic acid.

FIG. 8 shows the X-ray powder diffraction pattern of the meglumine salt of 2-((1R,4R)-4-(4-(5-(benzo[d]oxazol-2-ylamino)pyridin-2-yl)phenyl)cyclohexyl)acetic acid Polymorph Form H.

FIG. 9 is a TG/DTA thermograph of polymorph Form H of the meglumine salt of 2-((1R,4R)-4-(4-(5-(benzo[d]oxazol-2-ylamino)pyridin-2-yl)phenyl)cyclohexyl)acetic acid.

DETAILED DESCRIPTION

Definitions of various terms which are used herein are listed below.

A particular solid state salt form of the compound of formula (I) may be referred to as "crystalline form X", "crystal form X", "polymorph form X", where 'X' is the letter which is assigned to that particular solid state form.

The term "solid state form" and the term "crystalline form" as used herein include reference to anhydrous crystalline forms, partially crystalline forms, mixture of crystalline forms, hydrate crystalline forms and solvate crystalline forms.

The term "hydrate" as used herein refers to a crystalline form containing one or more water molecules in a three-dimensional periodic arrangement. It can include non-stoichiometric hydrates or stoichiometric hydrates, such as hemihydrates, monohydrates, dihydrates and trihydrates.

The term "solvate" as used herein refers to a crystalline form containing one or more solvent molecules other than water in a three-dimensional periodic arrangement.

The term "compound of the invention" refers to a salt of formula (I), preferably in crystalline form, such as a crystalline form of formula (Ia), preferably Forms as described in the Examples. It includes anhydrous crystalline forms, partially crystalline forms, mixtures of crystalline forms, hydrate crystalline forms and solvate crystalline forms.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The present invention includes all crystalline and pharmaceutically acceptable isotopically-labelled forms of the compound of formula (I). In an isotopically-labelled form, one or more atoms are replaced by an atom or atoms having the same atomic number, but an atomic mass or mass number different from the atomic mass or mass number which predominates in nature. Suitable isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O. Certain isotopically-labelled compounds, such as those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds can generally be prepared by conventional techniques known to those skilled in the art or by processes analogous to those described in the accompanying Examples and Preparations using an appropriate isotopically-labeled reagent in place of the non-labeled reagent previously employed.

As used throughout the specification and in the claims, the term "treatment" embraces all the different forms or modes of treatment as known to those of the pertinent art and in particular includes preventive, curative, delay of progression and palliative treatment.

Solid State Physical Properties

Polymorphism is the ability of a compound to crystallize in more than one distinct crystal species.

Pseudopolymorphism is the name given to solvates or hydrates, when a new crystal form contains a volatile solvent within its molecular packing.

Different crystalline or amorphous forms may exhibit different solid state physical properties such as hygroscopicity, behaviour on compaction, stability during storage, and flowability of the milled solid. These properties in turn affect the suitability of a particular solid state form as an active pharmaceutical for commercial production. For example, flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Different crystal forms or amorphous forms of the same drug may also have substantial differences in such pharmaceutically important properties as dissolution rates and bioavailability. Dissolution rates are not only a consideration in formulating syrups, elixirs and other liquid medicaments, they may also have therapeutic consequences. For example, the rate of dissolution of an active ingredient in a patient's stomach fluid can have therapeutic consequences since it imposes an upper limit on the rate at which an orally-administered active ingredient can reach the patient's bloodstream.

These practical physical characteristics are influenced by the conformation and orientation of molecules in the unit cell, which defines a particular polymorphic form of a substance. The polymorphic form may also give rise to thermal behaviour different from that of the amorphous material or another polymorphic form. Thermal behaviour is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by single-crystal or powder X-ray crystallography, solid state $^{13}$C NMR and $^{19}$F NMR spectrometry and infrared spectrometry. Methods used to characterize the crystal form also include infrared spectroscopy and melting point determination.

COMPOUNDS OF THE INVENTION

In one aspect, the present invention provides a salt of 2-((1R,4R)-4-(4-(5-(benzo[d]oxazol-2-ylamino)pyridin-2-yl)phenyl)cyclohexyl)acetic acid (formula I). In one embodiment, the salt of a compound of formula (I) is a meglumine salt represented by formula (Ia).

In another aspect, the present invention provides a crystalline form of the meglumine salt of 2-((1R,4R)-4-(4-(5-(benzo[d]oxazol-2-ylamino)pyridin-2-yl)phenyl)cyclohexyl)acetic acid represented by formula (Ia).

In one embodiment, the crystalline form is selected from the various crystalline forms detailed herein, each of which are characterised by an X-ray diffraction pattern with peaks substantially the same as depicted in the Figures. Alternatively, each modification is characterised by an X-ray diffraction pattern with characteristic peaks as set forth in its corresponding Table. In further embodiments, the present invention provides any of the crystalline forms of a salt of the compound of formula (I) or the compound of formula (Ia) as described herein, wherein the angle variation is +/−0.3° 2-theta, or +/−0.2° 2-theta or +/−0.15° 2-theta.

In one embodiment, the invention provides a crystalline form of a compound of formula (Ia), wherein the form is Form A characterized in that said form has at least one of the following characteristics:
  a) an X-ray powder diffraction pattern with two or more peaks (preferably three peaks, more preferably all peaks) at degrees two theta (±0.1 degree) as shown in Table 1;
  b) an X-ray powder diffraction pattern substantially in accordance with that shown in FIG. 1;
  c) a thermal gravimetric analysis curve substantially in accordance with that shown in FIG. 2; or In one embodiment, the invention provides a crystalline form of a compound of formula (Ia), wherein the form is Form B characterized in that said form has at least one of the following characteristics:
  a) an X-ray powder diffraction pattern with two or more peaks (preferably three peaks, more preferably all peaks) at degrees two theta (±0.1 degree) as shown in Table 2;
  b) an X-ray powder diffraction pattern substantially in accordance with that shown in FIG. 3; or
  c) a thermal gravimetric analysis curve substantially in accordance with that shown in FIG. 4.

In one embodiment, the invention provides a crystalline form of a compound of formula (Ia), wherein the form is Form C characterized in that said form has at least one of the following characteristics:
  a) an X-ray powder diffraction pattern with two or more peaks (preferably three peaks, more preferably all peaks) at degrees two theta (±0.1 degree) as shown in Table 3;
  b) an X-ray powder diffraction pattern substantially in accordance with that shown in FIG. 5;
  c) a differential scanning calorimetry curve substantially in accordance with that shown in FIG. 6; or
  d) a thermal gravimetric analysis curve substantially in accordance with that shown in FIG. 7;

In one embodiment, the invention provides a crystalline form of a compound of formula (Ia), wherein the form is Form H characterized in that said form has at least one of the following characteristics:

a) an X-ray powder diffraction pattern with two or more peaks (preferably three peaks, more preferably all peaks) at degrees two theta (±0.1 degree) as shown in Table 4; or b) an X-ray powder diffraction pattern substantially in accordance with that shown in FIG. 8.

c) a thermal gravimetric analysis curve substantially in accordance with that shown in FIG. 9;

In a further aspect of the invention, there is provided a substantially pure form of each crystalline form. Preferably each crystalline form is provided in 80, 85, 90, 95% or 99% pure form.

In a further aspect, the present invention provides a hydrate or a semi-hydrate of the compound of formula (Ia).

Routes of Administration and Pharmaceutical Formulations

In another aspect, the invention provides a pharmaceutical composition comprising a salt of 2-((1R,4R)-4-(4-(5-(benzo[d]oxazol-2-ylamino)pyridin-2-yl)phenyl)cyclohexyl) acetic acid (formula I), and one or more pharmaceutically acceptable carrier or excipient. In one embodiment, the salt of a compound of formula (I) is a meglumine salt represented by formula (Ia).

In another aspect, the invention provides a pharmaceutical composition comprising a crystalline form of the meglumine salt of 2-((1R,4R)-4-(4-(5-(benzo[d]oxazol-2-ylamino)pyridin-2-yl)phenyl)cyclohexyl)acetic acid represented by formula (Ia). In one embodiment, the crystalline form is Form A. In another embodiment, the crystalline form is Form B. In another embodiment, the crystalline form is Form C. In another embodiment, the crystalline form is Form H.

The compounds of the invention will normally be administered orally, intravenously, subcutaneously, buccally, rectally, dermally, nasally, tracheally, bronchially, by any parenteral route, as an oral or nasal spray or via inhalation. Parenteral modes of administration include intravenous, intramuscular, intraperitoneal, intrasternal, subcutaneous and intraarticular injections and infusions. Pharmaceutical compositions suitable for the delivery of the compounds of the invention and methods for their preparation may be found, e.g. *Remington's Pharmaceutical Sciences*, 19$^{th}$ Edition, (Mack Publishing Company, 1995).

The compounds of the invention may be administered orally. Advantageously, the compounds of the invention may be orally active, have rapid onset of activity and low toxicity. Oral administration may involve swallowing, so that the compound enters the gastrointestinal tract, or buccal or sublingual administration may be employed by which the compound enters the blood stream directly from the mouth.

Examples of formulations suitable for oral administration are solid formulations such as tablets, capsules containing particulates, liquids, or powders, lozenges (including liquid-filled), chews, multi- and nano-particulates, gels, solid solution, liposome, films, ovules, sprays and liquid formulations.

Examples of liquid formulations include suspensions, solutions, syrups and elixirs. These may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The compounds may be administered alone or as compositions in combination with pharmaceutically acceptable diluents, excipients or carriers. The present invention thus provides a pharmaceutical composition comprising a therapeutically effective amount of a compound of the invention, alone or in combination with one or more pharmaceutically acceptable carriers (excipients).

Examples of such carriers or excipients include:

a) a diluent, e.g., lactose, dextrose, sucrose, mannitol, sorbitol, cellulose and/or glycine;

b) a lubricant, e.g., silica, talcum, stearic acid, its magnesium or calcium salt and/or polyethyleneglycol;

c) a binder, e.g., magnesium aluminum silicate, starch paste, gelatin, tragacanth, methylcellulose, sodium carboxymethylcellulose and or polyvinylpyrrolidone;

d) a disintegrant, e.g., starches, agar, alginic acid or its sodium salt, or effervescent mixtures; and/or e) an absorbent, a colorant, a flavor and/or a sweetener.

Additional examples of useful excipients are described in the Handbook of pharmaceutical excipients, 3rd edition, Edited by A.HOURS.Kibbe, Published by: American Pharmaceutical Association, Washington D.C., ISBN: 0-917330-96-X, or Handbook of Pharmaceutical Excipients (4$^{th}$ edition), Edited by Raymond C Rowe—Publisher: Science and Practice which are incorporated herewith by reference.

Depending upon the disorder and patient to be treated and the route of administration, the compositions may be administered at varying doses. In general, the daily dose range of the compound of the invention lies within the range of from about 0.0001 mg/kg to about 100 mg/kg, preferably from about 0.001 mg/kg to about 50 mg/kg body weight of a subject in single or divided doses. On the other hand, it may be necessary to use dosages outside these limits in some cases.

In the case where an oral composition is employed, a suitable dosage range of the compound of the invention is, e.g. from about 0.001 mg/kg to about 100 mg/kg body weight of a subject in the composition per day, preferably from about 0.01 mg to about 2000 mg per day. For oral administration, the compositions are preferably provided in the form of tablets containing from 0.01 mg to 2,000 mg, e.g. 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850, 1,000 and 2,000 milligrams of the active ingredient for the symptomatic adjustment of the dosage to the subject to be treated. This dosage regimen may be adjusted to provide the optimal therapeutic response.

In general, for treating and/or preventing diabetes, diabetes associated with obesity, a diabetes related disorder, obesity and an obesity related disorder, the DGAT1 inhibitor in the combination is administered at a daily dosage of from about 0.0001 mg/kg to about 100 mg/kg of body weight, preferably from about 0.001 mg/kg to about 50 mg/kg, given in a single dose or in divided doses two to six times per day, or in sustained release form. The dosage regimen may be adjusted to provide the optimal therapeutic response.

The present invention further provides a pharmaceutical composition, preferably a tablet or a gelatine capsule, as herein described, comprising a second active ingredient (i.e. combination partner) as described below in the 'Combination therapy' section.

Accordingly, the present invention provides a pharmaceutical composition as described herein as for use as a medicament. A pharmaceutical composition as described herein is also provided for use in the treatment of a disorder or a condition associated with DGAT1 activity. A pharmaceutical composition as described therein for the manufacture of a medicament for the treatment of a disorder or a condition associated with DGAT1 activity is also provided.

A method of preventing or treating a disorder or a condition associated with DGAT1 activity comprising administrating a therapeutically effective amount of the composition to a subject in need of such a treatment is also provided.

Uses

As described herein above, the compounds of the present invention may be useful for the treatment or prevention of a disorder or a condition mediated by DGAT1 activity in animals, particularly humans.

Thus the present invention also provides a method for treating or preventing a condition or a disorder associated with DGAT1 activity, which method comprises administering a therapeutically effective amount of the compound of the invention to a subject in need thereof.

Thus the present invention provides the use of a compound of the invention, alone or in combination with another therapeutic agent (see below) for the manufacture of a medicament for treating or preventing a conditions or a disorder associated with DGAT1 activity in animals, particularly humans. A compound of the invention, alone or in combination with another therapeutic agent (see below) is also provided for use in treating or preventing a condition or a disorder associated with DGAT1 activity in animals, particularly humans.

Conditions or disorders associated with DGAT1 activity include metabolic disorders such as obesity, diabetes (type 1 or type 2), anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, chylomicronemia, familial chylomicronemia syndrome, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the present invention provides methods of using a compound or composition of the invention as an anorectic.

In one preferred embodiment, the condition or disorder associated with DGAT1 activity is impaired glucose tolerance, Type 2 diabetes, or obesity.

In another preferred embodiment, the condition or disorder associated with DGAT1 activity is hypercholesterolemia, hyperlipidemia, dyslipidemia, mixed dyslipidemia, or hypertriglyceridemia.

In another preferred embodiment, the condition or disorder associated with DGAT1 activity is chylomicronemia or familial chylomicronemia syndrome.

Combination Therapies

The treatment of prevention of the DGAT1-related a disorder or a condition listed above consists of administering to a subject in need thereof a therapeutically effective amount of a compound described in this invention. The treatment may also include the administration of a therapeutically effective amount of a compound of the invention and a therapeutically effective amount of at least one further pharmaceutically active compound. Accordingly, the invention provides a pharmaceutical composition comprising a compound of the invention and at least one additional therapeutic agent. The combination may also be administered simultaneously or sequentially in any order, separately or in a fixed combination (e.g. in the same pharmaceutical composition).

In particular, a composition or product of the invention may further comprise a therapeutic agent selected from:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; F×R (farnesoid×receptor) and L×R (liver×receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant;

d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; -adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors, and.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

The weight ratio of the compound of the present invention to the further active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. The herein described daily dosages are conveniently administered once (once a day administration) or in divided dosages (e.g. divided for a twice daily administration).

The present invention also relates to the use of a combination as hereinabove described for the manufacture of a medicament for treating or preventing a condition or a disorder associated with DGAT1 activity in animals, particularly humans. A combination as herein above described for use in the treatment or prevention of a condition or disorder associated with DGAT1 activity in animals, particularly humans. is also provided.

The present invention also provides a method for treating or preventing a condition or a disorder associated with DGAT1 activity, which method comprises administering daily to a subject in need thereof a combination as hereinabove described.

In accordance with the foregoing the present invention also provides a therapeutic combination, e.g., a kit, kit of parts, e.g., for use in any method as defined herein, comprising a compound of the invention, to be used concomitantly or in sequence with at least one pharmaceutical composition comprising at least another therapeutic agent, preferably selected from anti-diabetic agents, hypolipidemic agents, anti-obesity agents and anti-hypertensive agents. The kit may comprise instructions for its administration. The combination can be a fixed combination (e.g. in the same pharmaceutical composition) or a free combination (e.g. in separate pharmaceutical compositions).

Likewise, the present invention provides a method as defined above comprising co-administration, e.g., concomitantly or in sequence, of a therapeutically effective amount of a compound as defined in the claims and described above, or a pharmaceutically acceptable salt thereof, and a second drug substance, said second drug substance being an anti-diabetic, a hypolipidemic agent, an anti-obesity agent or an anti-hypertensive agent, e.g., as indicated above.

EXAMPLES

The following abbreviations are used herein.

| | |
|---|---|
| L | Liter |
| LOD | Loss on drying |
| mL | milliliter |
| r.h. | Relative humidity |
| TG/DTA | Thermogravimetric/Differential Thermal Analysis |
| DSC | Differential Scanning Calorimetry |
| XRPD | Poweder X-Ray Diffraction |
| THF | Tetrahydrofuran |
| DMSO | Dimethylsulfoxide |
| MEK | Methyl Ethyl Ketone |
| TBME | Methyl Tertiary Butyl Ether |
| MTBE | Methyl Tertiary Butyl Ether |
| MeOH | Methanol |
| h | Hour |
| hrs | Hours |
| Mg | milligram |

Other abbreviations used are those conventional in the art.
Methodology, Instruments and Standards Used
i) Powder X-Ray Diffraction (PXRD)
Powder X-ray diffraction patterns were determined using a Bruker D8 Discovery diffractometer under the following conditions:

| |
|---|
| Instrument: Bruker D8 Discovery |
| Irradiation: CuK1α(40 kV, 40 mA) |
| $CuK_1$ = 1.540598 Å |
| Scan range 3°-40° (2 theta value) |
| Scan type: 2theta scan/detector scan (HI-STAR detector) |
| Step time 180 seconds per frame |
| Step size 0.02deg |

XRPD profiles for the respective solid forms are shown in the Figures.

List of characteristic peaks are listed herein in the Tables below and described in the Figures.

As will be appreciated by the skilled person, the relative intensities of the various peaks within the Tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Tables. The skilled person will also appreciate that measurements using a different wavelength will result in different shifts according to the Bragg equation– $n\lambda=2d \sin \theta$, Such alternative PXRD patterns generated by use of alternative wavelengths are nevertheless representations of the same material.

ii) Thermogravimetric/Differential Thermal Analysis (TG/DTA)

| | |
|---|---|
| Instrument | Seiko TG/DTA |
| Temperature range | rt-295° C. |
| Scan rate | 10°/min |
| Nitrogen flow | 100 ml/min |

As will be understood by persons skilled in the art, slight variations in observed peaks are expected based on the specific spectrometer employed and the analyst's sample preparation technique. Some margin of error is present in each of the peak assignments reported above. The margin of error in the foregoing peak assignments is about ±1 cm$^{-1}$.

Example 1

Preparation of the Meglumine salt of 2-((1R,4R)-4-(4-(5-(benzo[d]oxazol-2-ylamino)pyridin-2-yl)phenyl)cyclohexyl)acetic acid Form A To the clear solution of 255.6 mg meglumine in 0.9 ml of DMSO at 50° C., 2-((1R,4R)-4-(4-(5-(benzo[d]oxazol-2-ylamino)pyridin-2-yl)phenyl)cyclohexyl)acetic acid solution of 560.1 mg 2-((1R,4R)-4-(4-(5-(benzo[d]oxazol-2-ylamino)pyridin-2-yl)phenyl)cyclohexyl) acetic acid in 7 ml THF was added. The clear solution turned cloudy at the end of addition. The solution was heated at 50° C. and more precipitate was observed. 15 ml MEK was added, then the solid was filtered and dried under vacuum.

An X-ray powder diffraction pattern of the meglumine salt of 2-((1R,4R)-4-(4-(5-(benzo[d]oxazol-2-ylamino)pyridin-2-yl)phenyl)cyclohexyl)acetic acid Form A obtained by the above procedure was determined (FIG. 1). The most significant peaks in the XRPD are shown in Table 1.

TABLE 1

List of most significant XRPD peaks for the meglumine salt of 2-((1R,4R)-4-(4-(5-(benzo[d]oxazol-2-ylamino)pyridin-2-yl)phenyl)cyclohexyl)acetic acid Form A.

| Angle 2-Theta ° | Intensity % |
|---|---|
| 8.331 | 17.1 |
| 10.152 | 23.8 |
| 11.489 | 16.8 |
| 12.797 | 31.3 |
| 14.008 | 45.3 |
| 15.081 | 36.8 |
| 15.814 | 80 |
| 16.594 | 38.9 |
| 17.235 | 47.8 |
| 18.629 | 63.9 |
| 19.487 | 40.3 |
| 20.421 | 43.4 |
| 20.76 | 34.4 |
| 21.893 | 100 |
| 22.583 | 24.4 |
| 23.36 | 14.8 |
| 24.718 | 20.4 |
| 25.741 | 34.8 |
| 26.661 | 18.4 |
| 27.316 | 16 |
| 28.672 | 19 |
| 29.386 | 13.1 |
| 31.73 | 19.8 |
| 34.096 | 14.4 |
| 36.997 | 11.9 |

Example 1A

Large scale preparation of the Meglumine salt of 2-((1R,4R)-4-(4-(5-(benzo[d]oxazol-2-ylamino)pyridin-2-yl)phenyl)cyclohexyl)acetic acid Form A 80.0 g of 2-((1R,4R)-4-(4-(5-(benzo[d]oxazol-2-ylamino)pyridin-2-yl)phenyl)cyclohexyl)acetic acid free acid, 37.6 g N-methylglucamine, 920 mL MeOH and 920 mL THF were added to a 3-L 4-necked flask (mechanical stirring), then heated slowly to 61.5° C. over 30 min and maintained at 61-62° C. (refluxing) for 2 h to give a stirrable suspension. The contents were cooled to 45° C. and 920 mL TBME was added at 45 to 35° C. over 5 min, and then stirred the at 15-17° C. for 30 min. The solids were filtered and the flask and filter cake were washed with 1×517 mL TBME. The filtered material was transferred into a 3-L 4-necked flask. 1.2 L MeOH was added and the mixture was heated at 60° C. for 1 h. The mixture was concentrated at 50° C. under house vacuum to a thick slurry (~622 mL volume, 622 g weight). 1.125 L TBME was added at 50 to 40° C. over 15 min. The suspension was cooled to 15° C. over 30 min and the solids were filtered. The flask and filter cake was washed with 1×180 mL TBME and then dried in a vacuum oven (70° C.) for 16 h to give 110.0 g beige solid.

Example 2

Preparation of the meglumine salt of 2-((1R,4R)-4-(4-(5-(benzo[d]oxazol-2-ylamino)pyridin-2-yl)phenyl)cyclohexyl)acetic acid Form B To 100 mL of THF and 5 mL of water was added 4.5 g of 2-((1R,4R)-4-(4-(5-(benzo[d]oxazol-2-ylamino)pyridin-2-yl)phenyl)cyclohexyl)acetic acid and 4.65 g of (DL)-camphorsulfonic acid. The mixture was heated to 60° C., became a brown solution and cooled to room temperature. The filtrate was collected and rinsed with THF, then added to a solution of 3.91 g of meglumine (2:1 meglumine: 2-((1R,4R)-4-(4-(5-(benzo[d]oxazol-2-ylamino)pyridin-2-yl)phenyl)cyclohexyl)acetic acid molar ratio) in 9 mL of water which was obtained by heating to 30° C. and cooling to room temperature. The solution was concentrated to 50 g, 110 mL of ethanol added and then concentrated to 80 g. 120 mL of ethanol was added then concentrated to 77 g. 110 mL of ethanol added, stirred for 70 C for 1 hour and then cooled to room temp. The suspension was filtered, washed with ethanol (2×20 mL) and dried in an over (60° C.) for 15 hrs.

An X-ray powder diffraction pattern of the meglumine salt of 2-((1R,4R)-4-(4-(5-(benzo[d]oxazol-2-ylamino)pyridin-2-yl)phenyl)cyclohexyl)acetic acid Form B obtained by the above procedure was determined (FIG. 3). The most significant peaks in the XRPD are shown in Table 2.

TABLE 2

List of most significant XRPD peaks for the meglumine salt of 2-((1R,4R)-4-(4-(5-(benzo[d]oxazol-2-ylamino)pyridin-2-yl)phenyl)cyclohexyl)acetic acid.

| Angle 2-Theta ° | Intensity % |
|---|---|
| 4.671 | 96.6 |
| 6.913 | 100 |
| 9.25 | 13.4 |
| 11.409 | 13.7 |
| 14.143 | 17.7 |
| 15.456 | 27.7 |
| 18.023 | 32.6 |
| 20.6 | 20.6 |
| 23.786 | 18.5 |
| 25.516 | 21.1 |
| 27.42 | 14 |

Example 3

Preparation of the meglumine salt of 2-((1R,4R)-4-(4-(5-(benzo[d]oxazol-2-ylamino)pyridin-2-yl)phenyl)cyclohexyl)acetic acid Form C 15.37 kg of 2-((1R,4R)-4-(4-(5-(benzo[d]oxazol-2-ylamino)pyridin-2-yl)phenyl)cyclohexyl)acetic acid is mixed with 7.52 kg N-methylglucamine and dissolved in the mixture of 331 kg THF and 41 kg H$_2$O at 55° C. The resulting clear solution is held at 55° C. for at least 30 minutes to ensure the completion of dissolution. The solution is clear filtered. The clear solution is concentrated under house vacuum at 50° C. jacket temperature (T$_j$). To the resulting slurry (~92 L), 284 kg methanol is added and concentrated under house vacuum at T$_j$=50° C. The thick slurry (~150 L) obtained is diluted with 180 kg methanol and held at 50° C. for 1 hr. The slurry is then cooled to 40° C. and 142 kg MTBE is added. The slurry is held at 40° C. for at least 30 minutes and cooled to 15° C. over at least 50 minutes. The product is then filtered and washed with MTBE and dried to give 21.6 kg (94% yield) of 2-((1R,4R)-4-(4-(5-(benzo[d]oxazol-2-ylamino)pyridin-2-yl)phenyl)cyclohexyl)acetic acid meglumine Form C.

An X-ray powder diffraction pattern of the meglumine salt of 2-((1R,4R)-4-(4-(5-(benzo[d]oxazol-2-ylamino)pyridin-2-yl)phenyl)cyclohexyl)acetic acid Form C obtained by the above procedure was determined (FIG. 5). The most significant peaks in the XRPD are shown in Table 3.

TABLE 3

List of most significant XRPD peaks for the meglumine salt of 2-((1R,4R)-4-(4-(5-(benzo[d]oxazol-2-ylamino)pyridin-2-yl)phenyl)cyclohexyl)acetic acid.

| Angle 2-Theta ° | Intensity % % |
|---|---|
| 4.064 | 100 |
| 6.095 | 28 |
| 8.082 | 40.2 |
| 12.157 | 16.3 |
| 14.195 | 16.4 |
| 15.307 | 65.2 |
| 16.492 | 32.1 |
| 17.37 | 36.9 |
| 18.407 | 42.7 |
| 19.67 | 59.6 |
| 20.875 | 31.8 |
| 22.308 | 35.4 |
| 23.287 | 25 |
| 23.748 | 39.2 |
| 24.784 | 34.7 |
| 25.445 | 38.4 |
| 26.486 | 31.1 |
| 28.286 | 20.5 |
| 30.185 | 20.7 |
| 30.752 | 26.6 |
| 32.385 | 24 |
| 33.156 | 15.7 |
| 35.752 | 15.9 |

Example 3A

Preparation of the meglumine salt of 2-((1R,4R)-4-(4-(5-(benzo[d]oxazol-2-ylamino)pyridin-2-yl)phenyl)cyclohexyl)acetic acid Form A from Form C Add 100 g 2-((1R,4R)-4-(4-(5-(benzo[d]oxazol-2-ylamino)pyridin-2-yl)phenyl)cyclohexyl)acetic acid meglumine Form C in a 2-L Argonaut reactor, add a solution of 9.2 g meglumine in 1.9 L MeOH into the reactor through a line-filter, then rinse the filtrate with 1×100 mL MeOH. Stir the suspension at 25° C. mechanically for 16 h, filter ~10 mL mixture at 20° C., rinse the cake at 20° C. with 4 mL MeOH/TBME (1/1), and then dry the filter cake at 50° C. (house vacuum) for 10 min. Cool the slurry to 20° C. and hold for 30 min, filter solids through a Buchner funnel (6.5" diameter) and filter pad (fast filtration), then wash the reactor and filter cake with 1×700 mL MeOH/TBME (1/1, v/v). Air-dry the cake for 2 h, then dry solid cake in a vacuum oven (65° C., 35 mbar) for 16 h to give 92.0 g off-white solid 2-((1R,4R)-4-(4-(5-(benzo[d]oxazol-2-ylamino)pyridin-2-yl)phenyl)cyclohexyl)acetic acid meglumine Form A in 92.0% yield.

Example 4

Preparation of the meglumine salt of 2-((1R,4R)-4-(4-(5-(benzo[d]oxazol-2-ylamino)pyridin-2-yl)phenyl)cyclohexyl)acetic acid Form H Approximately 100 mg of 2-((1R,4R)-4-(4-(5-(benzo[d]oxazol-2-ylamino)pyridin-2-yl)phenyl)cyclohexyl)acetic acid meglumine Form A was granulated with water by hand in a mortar and pestle for 2 minutes, dried, and analyzed by XRPD and TG/DTA.

An X-ray powder diffraction pattern of the meglumine salt of 2-((1R,4R)-4-(4-(5-(benzo[d]oxazol-2-ylamino)pyridin-2-yl)phenyl)cyclohexyl)acetic acid Form H obtained by the above procedure was determined (FIG. 4). The most significant peaks in the XRPD are shown in Table 4.

TABLE 4

List of most significant XRPD peaks for the meglumine salt of 2-((1R,4R)-4-(4-(5-(benzo[d]oxazol-2-ylamino)pyridin-2-yl)phenyl)cyclohexyl)acetic acid Form H.

| Angle 2-Theta ° | Intensity % % |
|---|---|
| 5.142 | 55.8 |
| 7.58 | 23.8 |
| 8.317 | 23.9 |
| 10.184 | 27.6 |
| 12.864 | 32.9 |
| 14.052 | 73 |
| 15.196 | 41.4 |
| 15.918 | 50.2 |
| 16.765 | 33.6 |
| 17.416 | 44.1 |
| 18.191 | 68.6 |
| 18.882 | 49.7 |
| 19.789 | 46.3 |
| 20.76 | 33.8 |
| 21.943 | 100 |
| 23.341 | 29.5 |
| 24.319 | 81 |
| 25.793 | 36.3 |
| 27.199 | 25.9 |
| 28.722 | 20.4 |

Example 5

2-((1R,4R)-4-(4-(5-(benzo[d]oxazol-2-ylamino)pyridin-2-yl)phenyl)cyclohexyl) acetate sodium salt 16.41 g 2-((1R,4R)-4-(4-(5-(benzo[d]oxazol-2-ylamino)pyridin-2-yl)phenyl)cyclohexyl)acetic acid methyl ester, 50 ml methanol, 500 ml tetrahydrofuran and 136 ml water were added in 1 L flask with stirring bar. The mixture was cooled in ice bath, then 7.44 g sodium hydroxide was added. The reaction mixture was stirred for 10 minutes, then the ice bath was removed. The reaction mixture was stirred for another 40 hours and then filtered. The filtrate was concentrated to a suspension under 70 torr in 25° C. water bath. 300 ml water was added to the suspension, and the suspension was stirred for 4 hours at room temperature. The suspension was then filtered; the filtered cake was washed with 200 ml water. The washed cake was dried in oven at 60° C. for 4 hours, then at 50° C. over weekend. 15.63 g (93.6% yield) of slightly yellowish solid was obtained.

Example 6

2-((1R,4R)-4-(4-(5-(benzo[d]oxazol-2-ylamino)pyridin-2-yl)phenyl)cyclohexyl) acetate Hemi-choline salt Mix 400 mg 2-((1R,4R)-4-(4-(5-(benzo[d]oxazol-2-ylamino)pyridin-2-yl)phenyl)cyclohexyl) acetate free acid in 6 ml THF and warm to 40° C. to form a thin slurry. Warm 283 mg of 40% choline in methanol solution to ~40° C. Mix the slurry with the choline solution in potion to obtain a yellow solution. After precipitation occurs, stir the slurry overnight at 45° to 50° C., and add 4 ml methyl ethyl ketone and 4 ml THF. Filter the slurry and dry the solid under vacuum at 40° C. overnight.

Example 7

2-((1R,4R)-4-(4-(5-(benzo[d]oxazol-2-ylamino)pyridin-2-yl)phenyl)cyclohexyl) acetate Potassium salt Mix 400 mg 2-((1R,4R)-4-(4-(5-(benzo[d]oxazol-2-ylamino)pyridin-2-yl)phenyl)cyclohexyl) acetate free acid in 6 ml THF and warm to ~40° C. to form a thin slurry. Dissolve 105 mg potassium tert-butoxide in 1 ml ethanol and 2 ml methanol at 40-50° C. After precipitation occurs, stir the slurry overnight at 45° to 50° C., and add 4 ml methyl ethyl ketone and 4 ml THF. Filter the slurry and dry the solid under vacuum at 40° C. overnight.

Example 8

Physiochemical Properties (Stability and Solubility) of the different salt forms and free acid of 2-((1R,4R)-4-(4-(5-(benzo[d]oxazol-2-ylamino)pyridin-2-yl)phenyl)cyclohexyl)acetate

TABLE 5

Properties of crystalline forms of 2-((1R,4R)-4-(4-(5-(benzo[d]oxazol-2-ylamino)pyridin-2-yl)phenyl)cyclohexyl) acetate meglumine. All stability data, solubility data, physical properties and manufacturing parameters for 2-((1R,4R)-4-(4-(5-(benzo[d]oxazol-2-ylamino)pyridin-2-yl)phenyl)cyclohexyl)acetic acid. The Meglumine salt, Form A is the preferred physical form based on its favorably low hygroscopicity, good stability at ambient and stress conditions and morphic properties as compared to other studied salt forms. 2-((1R,4R)-4-(4-(5-(benzo[d]oxazol-2-ylamino)pyridin-2-yl)phenyl)cyclohexyl)acetic acid meglumine, Form A has comparable stability to the free acid form but has improved aqueous solubility over the free acid form. 2-((1R,4R )-4-(4-(5-(benzo[d]oxazol-2-ylamino)pyridin-2-yl)phenyl)cyclohexyl) acetate meglumine Form A is able to provide high exposure multiple (~150× the efficacious exposure) in both preclinical tox species (rat and dog) which is detailed in Example 9.

|  | Free acid | Sodium | Meglumine Form A | Hemi-choline | Potassium |
|---|---|---|---|---|---|
| Salt/base ratio | — | 1:1 | 1:1 | 0.5:1 | 1:1 + hydrate |
| Molecular Mass [g/mol] | 427.51 | 449.5 | 622.73 | 495.9 | 465.61 |
| Crystallinity (PXRD) | Crystalline | Crystalline | Crystalline | Crystalline | Crystalline |
| Melting Point (DSC) [° C.] | 287.4 | NA, multiple thermal events | 182.9 | 233 | NA, hydrate (possible monohydrate) |
| Enthalpy of melting (DSC) [J/g] | 152 | NA, multiple thermal events | 48 | NA, decomposes at melt | NA, multiple thermal events |
| Weight loss (TGA) [%] at 150° C. | 0.12 | 3.4 | 0.25 | 0.7 | 5.7 |
| Hygroscopicity [%] | | | | | |
| 0-40% r.h. | 0.136 | 13.1 | 0.162 | 1.44 | 4.52 |
| 0-95% r.h. | 0.251 | 16.2 | 0.588 | 15.95 | 21.77 |
| Change in crystallinity (PXRD) | No | No | No | No | No |
| Solubility [mg/ml] (pH final) | | | | | |
| pH 1 (0.1N HCl) | <0.0005 (1.59) | <0.0005 (1.03) | 0.15 (2.79) | 0.14 (1.06) | 0.05 (3.89) |
| pH 4.8 (50 mM Acetate) | <0.0005 (4.76) | <0.0005 (5.08) | <0.0005 (4.88) | 0.015 (4.76) | <0.0005 (4.90) |
| pH 6.5 (50 mM Phosphate) | <0.0005 (6.87) | 0.0006 (8.5) | 0.04 (7.27) | 0.03 (7.15) | <0.0005 (7.29) |
| SGF pH 2.0 | <0.0005 (2.38) | 0.062* (9.13) | <0.0005 (2.37) | 0.095 (1.05) | 0.003 (3.73) |
| FaSSIF V2 | 0.02 (6.34) | 0.007 (7.47) | 0.01 (6.86) | 0.34 (7.45) | 0.095 (8.32) |
| FeSSIF V2 | 0.06 (5.53) | 0.003 (5.66) | 0.001 (6.26) | n.d. (problem with filtration) | n.d. (problem with filtration) |
| Water | 0.01 (7.63) | 0.023 (9.3) | 0.07 (10.4) | 0.185 (9.77) | 1.05 (10.3) |

TABLE 5-continued

Properties of crystalline forms of 2-((1R,4R)-4-(4-(5-(benzo[d]oxazol-2-ylamino)pyridin-2-yl)phenyl)cyclohexyl) acetate meglumine. All stability data, solubility data, physical properties and manufacturing parameters for 2-((1R,4R)-4-(4-(5-(benzo[d]oxazol-2-ylamino)pyridin-2-yl)phenyl)cyclohexyl)acetic acid. The Meglumine salt, Form A is the preferred physical form based on its favorably low hygroscopicity, good stability at ambient and stress conditions and morphic properties as compared to other studied salt forms. 2-((1R,4R)-4-(4-(5-(benzo[d]oxazol-2-ylamino)pyridin-2-yl)phenyl)cyclohexyl)acetic acid meglumine, Form A has comparable stability to the free acid form but has improved aqueous solubility over the free acid form. 2-((1R,4R)-4-(4-(5-(benzo[d]oxazol-2-ylamino)pyridin-2-yl)phenyl)cyclohexyl) acetate meglumine Form A is able to provide high exposure multiple (~150× the efficacious exposure) in both preclinical tox species (rat and dog) which is detailed in Example 9.

| | Free acid | Sodium | Meglumine Form A | Hemi-choline | Potassium |
|---|---|---|---|---|---|
| Intrinsic Dissolution Rate [mg min$^{-1}$ cm$^{-2}$] | | | | | |
| pH 4.5 (50 mM Acetate) | 0.013 | n.d. | BLQ | BLQ | n.d. (salt expanded and collapsed; did not retain the specific unit area exposed) |
| pH 6.8 (50 mM Phosphate) | BLQ | n.d. | BLQ | n.d. (salt expanded and collapsed; did not retain the specific unit area exposed) | n.d. (salt expanded and collapsed; did not retain the specific unit area exposed) |

Example 9

Key in vivo data demonstrating advanced biopharmaceutical performance of 2-((1R,4R)-4-(4-(5-(benzo[d]oxazol-2-ylamino)pyridin-2-yl)phenyl) cyclohexyl)acetic acid meglumine Absolute oral bioavailability of 2-((1R,4R)-4-(4-(5-(benzo[d]oxazol-2-ylamino)pyridin-2-yl)phenyl)cyclohexyl)acetic acid meglumine from a 30 mg/kg solution dose (2-((1R,4R)-4-(4-(5-(benzo[d]oxazol-2-ylamino)pyridin-2-yl)phenyl)cyclohexyl)acetic acid sodium material dissolved in 10% HPβCD in purified water or PBS) in dog is 1.5%. At a similar dose, the solid dispersion formulation showed approximately 4-times higher exposure and an oral bioavailability of 5.4%. Upon dose escalation to 100 and 300 mg/kg with solid dispersion, the exposure increased almost linearly and oral bioavailability continued to be low (2-3%).

With a meglumine salt suspension at 100 mg/kg, about 33% decrease in plasma exposure was observed compared to solid dispersion. However, similar to rat, the efficacious AUC in dog for 2-((1R,4R)-4-(4-(5-(benzo[d]oxazol-2-ylamino) pyridin-2-yl)phenyl)cyclohexyl)acetic acid is very low (132 nM.hr at 0.3 mpk) and therefore, the meglumine salt suspension already provides ~150× higher exposures over the efficacious AUC and was therefore considered as a suitable approach for GLP toxicology studies. The solid dispersion formulation has several technical challenges which can be avoided by using a 2-((1R,4R)-4-(4-(5-(benzo[d]oxazol-2-ylamino)pyridin-2-yl)phenyl)cyclohexyl)acetic acid meglumine Form A suspension-based formulation.

Direct in vivo comparison of 2-((1R,4R)-4-(4-(5-(benzo[d]oxazol-2-ylamino)pyridin-2-yl)phenyl)cyclohexyl)acetic acid meglumine and 2-((1R,4R)-4-(4-(5-(benzo[d]oxazol-2-ylamino)pyridin-2-yl)phenyl)cyclohexyl)acetic acid sodium salt suspensions were performed in rat and mouse. The meglumine suspension at 30 mg/kg in mouse had 17.3% bioavailability versus only 9.6% for the sodium suspension. Likewise at 30 and 100 mg/kg the sodium suspension is not dose linear in rat demonstrating 7.6% and 4.6% bioavailability respectively. The meglumine salt is dose linear at 30 and 100 mg/kg (3.1% and 3.8% bioavailability) and only becomes non-linear at 300 mpk (1.9% bioavailability). From this preclinical data, it was confirmed that 2-((1R,4R)-4-(4-(5-(benzo[d]oxazol-2-ylamino)pyridin-2-yl)phenyl)cyclohexyl)acetic acid meglumine is a better performing salt.

A standard capsule formulation with 2-((1R,4R)-4-(4-(5-(benzo[d]oxazol-2-ylamino)pyridin-2-yl)phenyl)cyclohexyl)acetic acid meglumine is the recommended CSF strategy to support the projected efficacious dose range in human (11-120 mg) based on following observations:

- Low efficacious dose of 2-((1R,4R)-4-(4-(5-(benzo[d]oxazol-2-ylamino)pyridin-2-yl)phenyl)cyclohexyl)acetic acid in preclinical species (0.1-0.3 mg/kg)
- High exposure multiples in preclinical species (rat and dog) from a suspension formulation of 2-((1R,4R)-4-(4-(5-(benzo[d]oxazol-2-ylamino)pyridin-2-yl)phenyl)cyclohexyl)acetic acid meglumine
- Aqueous kinetic solubility of 2-((1R,4R)-4-(4-(5-(benzo[d]oxazol-2-ylamino)pyridin-2-yl)phenyl)cyclohexyl) acetic acid meglumine can be further improved (20-60 fold) from simple physical blend with polymers and/or surfactants
- Improvement in exposure and dose linearity from 2-((1R,4R)-4-(4-(5-(benzo[d]oxazol-2-ylamino)pyridin-2-yl) phenyl)cyclohexyl)acetic acid meglumine over the sodium salt

We claim:

1. A maglumine salt of 2-((1R,4R)-4-(4-(4-(5-(benzo[d] oxazol-2-ylamino)pyridin-2-yl)phenyl)cyclohexyl)acetic acid represented by formula (Ia):

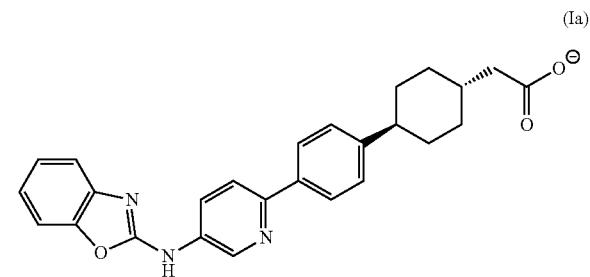

(Ia)

-continued
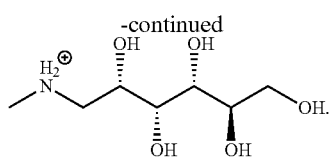
2. A pharmaceutical composition comprising the meglumine salt, according to claim 1, and one or more pharmaceutically acceptable carrier or excipient.
3. A composition according to claim 2 comprising an additional therapeutic agent.
* * * * *